United States Patent [19]

Grayzel

[11] Patent Number: 4,921,479
[45] Date of Patent: May 1, 1990

[54] CATHETER SHEATH WITH LONGITUDINAL SEAM

[76] Inventor: Joseph Grayzel, 262 Fountain Rd., Englewood, N.J. 07631

[21] Appl. No.: 104,279

[22] Filed: Oct. 2, 1987

[51] Int. Cl.⁵ ............................................. A61M 5/00
[52] U.S. Cl. ..................... 604/53; 604/160; 604/164; 604/280; 606/108
[58] Field of Search ...................... 128/1 D, 343, 345; 604/51–53, 158–171, 280

[56] References Cited

U.S. PATENT DOCUMENTS

| | | | |
|---|---|---|---|
| 3,401,687 | 9/1968 | Hood | 128/79 |
| 3,472,232 | 10/1969 | Earl | 604/160 |
| 3,559,643 | 2/1971 | Pannier et al. | 604/164 |
| 3,570,485 | 3/1971 | Reilly | 604/53 |
| 3,788,318 | 1/1974 | Kim et al. | 604/164 |
| 3,853,130 | 12/1974 | Sheridan | 604/171 |
| 3,921,631 | 11/1975 | Thompson | 604/53 |
| 4,243,050 | 1/1981 | Littleford | 604/164 X |
| 4,411,655 | 10/1983 | Schreck | 604/165 |
| 4,451,256 | 5/1984 | Weikl et al. | 604/343 X |
| 4,473,067 | 9/1984 | Schiff | 604/158 X |
| 4,498,902 | 2/1985 | Ash et al. | 604/164 |
| 4,569,347 | 2/1986 | Frisbie | 604/164 X |
| 4,581,025 | 4/1986 | Timmermans . | |
| 4,602,624 | 7/1986 | Naples et al. | 128/784 |
| 4,619,644 | 10/1986 | Scott | 604/53 |
| 4,629,450 | 12/1986 | Suzuki et al. | 604/164 |
| 4,645,491 | 2/1987 | Evans | 604/53 X |
| 4,693,249 | 9/1987 | Schenck et al. | 128/343 X |

FOREIGN PATENT DOCUMENTS 0206553 12/1986 European Pat. Off. ............ 604/280

Primary Examiner—Dalton L. Truluck
Attorney, Agent, or Firm—Weingram & Zall

[57] ABSTRACT

An improved removable expandable sheath for aiding in the introduction of catheters into the body which is fabricated from a semi-stiff plastic with memory formed in a tubular configuration with a longitudinal slit or non-joined seam extending along the entire length of the sheath and where the tubular structure with slit is coiled about its longitudinal axis so that its tubular wall overlaps itself in its native state. On exertion of an internal force directed outward, the tubular sheath enlarges its effective diameter by uncoiling to the extent necessary to accommodate a catheter inserted therein. The memory inherent in the material of the sheath keeps the wall of the sheath snugly around the catheter to afford guidance of the catheter into a blood vessel.

20 Claims, 4 Drawing Sheets

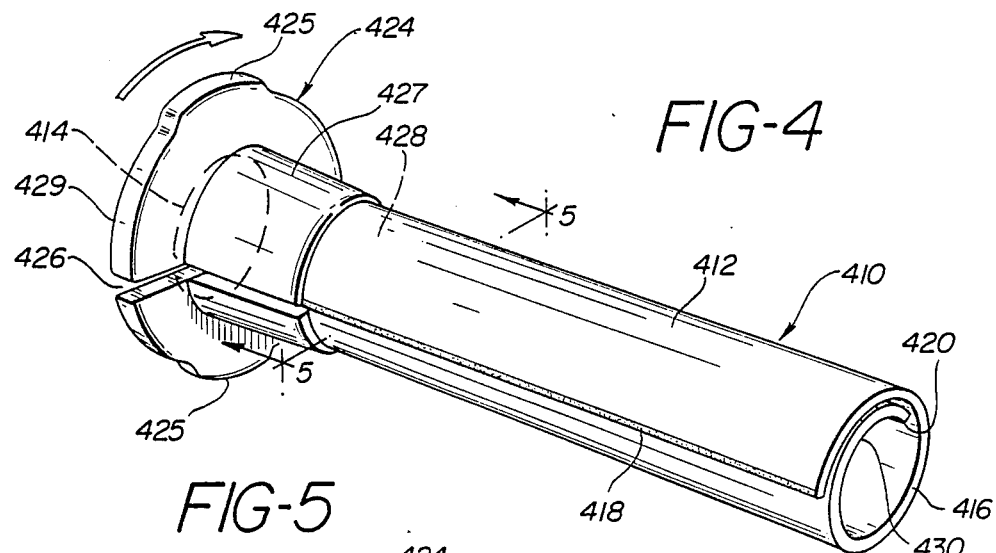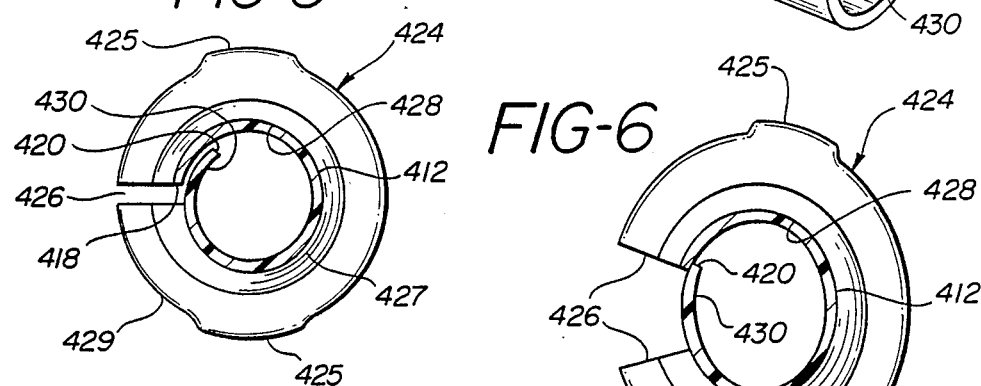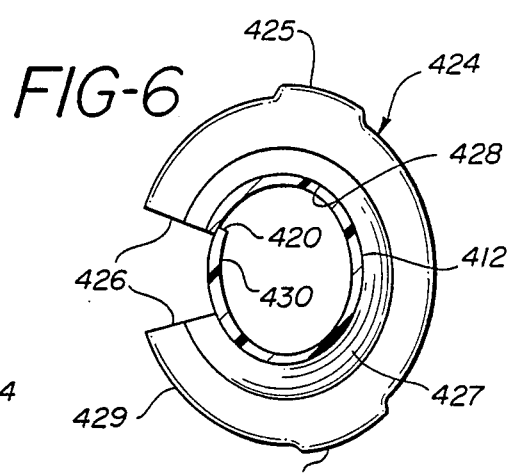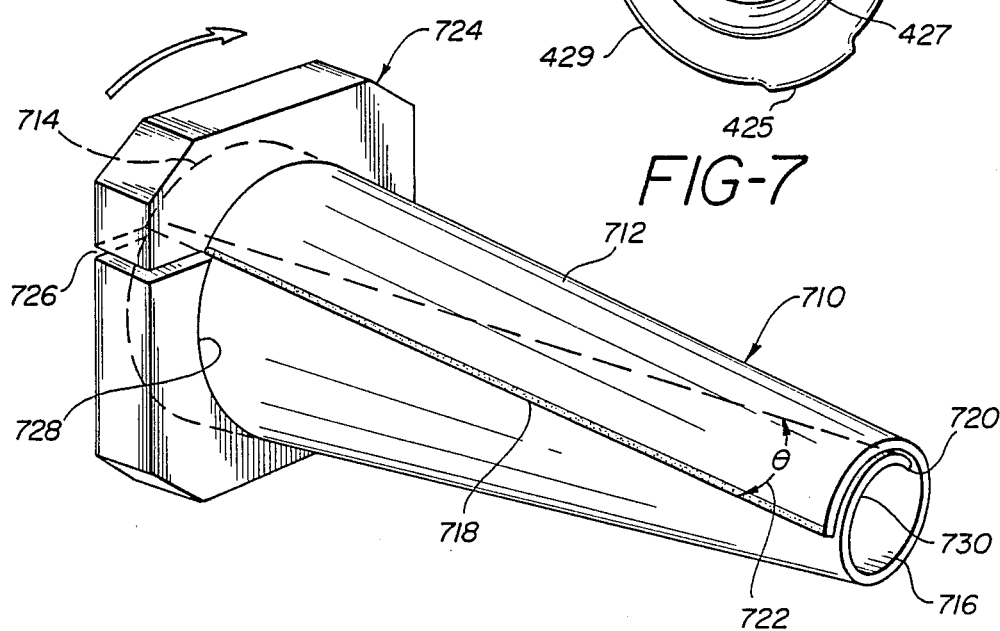

CATHETER SHEATH WITH LONGITUDINAL SEAM

BACKGROUND OF THE INVENTION

1. Field of the Invention

This invention relates to sheaths for use with catheters and more particularly to flexible sheaths used in the percutaneous method of introducing catheters.

2. Description of the Prior Art

Insertion of catheters into blood vessels is frequently accomplished percutaneously, a term indicating that surgical cut-down to the vessel is not employed, but rather the initial entry into the vessel is by direct needle puncture through the skin. Early practise employed the puncturing needle itself as a direct conduit to the blood vessel for a catheter of sufficiently small diameter to be passed inside the needle. At first, such catheters were of adequate length to permit the needle to be withdrawn entirely from the tissue yet remaining on the proximal portion of said catheter outside the human body. However, the needle so remaining on the catheter was often an impediment, hence the desirability of freeing the needle completely from the catheter was recognized.

Subsequent art developed the longitudinally split needle which separated into two distinct members. This was possible owing to the physical properties of steel, including strength, rigidity, and precise machinability so that minute mechanical features of the two parts enabled them to snap together or otherwise securely engage and capture one another in order to function as a one-piece needle.

The foregoing metallurgical and mechanical art was not applicable to thin-walled plastic sheaths, as subsequently used for the percutaneous insertion of large-diameter cardiovascular catheters according to the method of Seldinger as modified by Desilets and Hoffman described in Timmerman's U.S. Pat. No. 4,581,025. Therefore, such sheaths often remain in place during catheterization procedures, or may be drawn back along the catheter if removal from the puncture site is desired. However, the hub (e.g. LUER-LOK or bayonet fitting) at the proximal end of the catheter prevents removal of the sheath from the catheter itself.

In those instances where intravascular catheters remain in place for longer periods of time, or are to be permanently implanted as with pacemakers, it is desirable to remove the sheath completely. This led to the development by Littleford and others of the "peel-away" sheath, a very flexible and flaccid, thin-walled plastic tube without any proximal hub or fitting, whose proximal end was already bi-leaved so that grasping one such leaf in each hand and pulling apart caused the sheath to tear longitudinally along opposite lines and separate into two long strips. This sheath is described in Timmerman's U.S. Pat. No. 4,581,025. While accomplishing its objective of removing the sheath, it is a cumbersome method because both hands must grasp the sheath, leaving the catheter within said sheath unattended unless an assistant is present. Also once removed, another sheath cannot be inserted over the catheter if so desired.

Another disadvantage of the presently-used sheaths results from the fact that they are of fixed diameter. Thus, when percutaneous insertion is performed, a sheath is inserted which will accommodate the largest-diameter catheter needed during the procedure. Further, all catheters used during the procedure should match the diameter of the largest catheter needed, since the lumen of the sheath must be fully occupied to prevent excessive bleeding. For example, measurement of intracardiac blood pressure or injection of small volumes of radio-contrast dye into the coronary arteries can be adequately performed with a catheter of diameter significantly smaller than that needed for injection of a large volume of dye to visualize the left ventricle; thus, the greater portion of such a complex procedure could be performed via a small puncture hole, and only at the end of said procedure need the puncture hole be dilated, which so executed would reduce the degree and incidence of postprocedure bleeding. However, employing sheaths of fixed diameter only permit catheters of identical diameter to be deployed via said sheath.

Other patents which deal with sheaths include U.S. Pat. No. 3,401,687 to Hood which discloses a sexual aid for males comprised of an expansible unitary resilient member with overlapping ends. U.S. Pat. No. 4,581,025 to Timmermans teaches a tear away sheath of the type generally employed in the prior art. U.S. Pat. No. 4,602,624 to Naples et al. discloses a nerve cuff which uses a self-curling sheet of non-conductive material biased to curl into a tight spiral.

SUMMARY AND OBJECTS OF THE INVENTION

The present invention is an improved removable and expandable sheath fabricated from a semi-stiff plastic with memory, formed in a tubular configuration with a longitudinal slit or non-joined seam extending along the entire length, and further where the tubular structure with slit may be coiled about its longitudinal axis so that its tubular wall may overlap itself in its native state. On exertion of an internal force directed outward, the tubular sheath enlarges its effective diameter by uncoiling to the extent necessary to accommodate a catheter inserted therein, yet the memory inherent in the plastic keeps the wall of the sheath snugly around the catheter to afford guidance into the blood vessel.

An object of the invention is to provide a percutaneous sheath which is completely removable from the catheter and insertion site.

Another object of the invention is the provision of a sheath which, following its complete removal, may be replaced on the catheter and reinserted into the puncture site.

A further object of the present invention is to provide a percutaneous catheter sheath which may be removed by being grasped with only one hand.

A further object of the invention is to accomplish sheath removal without tearing or without the requirement to exert any significant force.

A further object of the invention is to provide a sheath of the class described which can be fabricated with a proximal hub or fitting such as LUER-LOK, bayonet or the like.

A still further object of the present invention is to provide an insertion sheath for catheters which may be formed by thermal, or other processes into a configuration which permits the diameter of the sheath to enlarge relative to its diameter at the time of its insertion percutaneously.

A yet further object of the invention is to provide a sheath which permits the use of catheters of different diameters to be inserted therein while maintaining hemostasis.

Another object of the present invention is to provide a sheath which can change its diameter momentarily, responsive to an expansile catheter.

Still another object of the present invention is to provide a sheath which can be made with a side arm for irrigation.

Another object of the present invention is to provide a sheath which has a bevelled tip for ease of insertion.

Yet another object of the present invention is to provide a sheath which in its native state is tapered, for ease of insertion, but with a cylindrical catheter inserted within the sheath will transform to a cylindrical shape.

A further object of the present invention is to provide a sheath which can change shape and dimension.

Another object of the present invention is to provide a sheath which can fit a wide range of catheter diameters.

Yet another object of the present invention is to provide a sheath which can change dimension during use to accommodate catheters of different dimension.

Still another object of the present invention is to provide an insertion sheath which is safer to use because it requires the use of only one hand for removal of the sheath.

Yet another object of the present invention is to provide an insertion sheath for use which is safer because it is self-adjusting and requires no external manipulation once installed and operatively positioned.

A further object of the present invention is to provide a connecting fitting for a sheath which can be opened up to allow for removal of an item positioned in the lumen of the sheath through the wall or a seam in the sheath and a slit in the connecting fitting.

Another object of the present invention is to provide a fitting for connecting a sheath to conduit means, which fitting is attached to the sheath and which allows for items to be inserted within the lumen of the sheath through a seam or slit in the wall of the sheath and the connecting fitting.

These as well as further object and avantages of the present invention will become apparent to those skilled in the art from a review of the accompanying detailed description of the preferred embodiment, reference being made to the accompanying drawings.

BRIEF DESCRIPTION OF THE DRAWINGS

FIG. 4 is a perspective view showing one embodiment of the invention with a coupling mechanism attached thereto;

FIG. 5 is a cross-section taken through lines 5—5 of FIG. 4;

FIG. 6 is a view similar to FIG. 5 showing the device in the expanded position;

FIG. 7 is another embodiment of the device similar to FIG. 4 but with a tapered sheath;

DESCRIPTION OF THE PREFERRED EMBODIMENT

The fundamental principle underlying the improved removable and expandable sheath described herein is its fabrication from a semi-stiff plastic with memory, formed in a tubular configuration with a longitudinal slit or non-joined seam extending its entire length, and where said tubular structure with slit is coiled about its longitudinal axis such that its tubular wall overlaps itself in its native state. Upon exertion of an internal force directed outward, as by insertion of a catheter whose diameter is larger than that of the native unstressed coil, said tubular sheath enlarges its effective diameter by uncoiling to the extent necessary to accommodate said catheter, yet the memory inherent in the plastic keeps the wall of the sheath snugly around said catheter to afford guidance into the blood vessel. Simple manipulation with one hand can allow for loosening or tightening the sheath as desired by the operator.

A hub, LUER-LOK, LUER-SLIP, or other mechanical fitting may be affixed to the proximal end of the sheath, but must be modified to cooperate with the expansile capability of said sheath. To do so, the circumferential fitting must have a longitudinal slit or parting line which is colinear with one edge of the longitudinal seam of the sheath. The circumference of the fitting corresponds to the circumference of the native unstressed sheath, and therefore that portion of the sheath's proximal circumference which underlaps within the coil is devoid of direct attachment or correspondence with said hub or fitting. As is the case for the sheath itself, the fitting must also be of a semiflexible plastic with memory.

The distal tip of the present sheath may be cut diagonally to form a bevel, in which case the leading edge of the bevel is located 180° opposite to the seam, the bevel tapers back from its leading edge at either side and the rearmost point of the bevel is at the longitudinal seam. The corner formed by the intersection of the bevel with the longitudinal seam is rounded to avoid any sharp point or angle at this juncture. The edges of the seam are marked by a colored stripe extending the entire length of said seam. The sheath is inserted with the seam uppermost and the stripe visible to the eye along the uppermost aspect of the cylindrical sheath, hence the leading point of the bevel is undermost.

Figure 1:
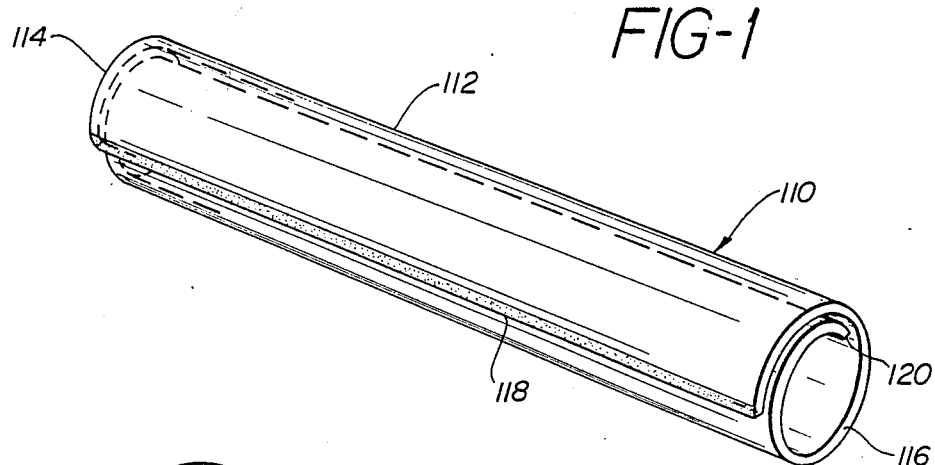
FIGS. 1-3 are perspective views of alternate embodiments of the invention.

The first embodiment, shown in FIG. 1, consists of a semi-rigid plastic tubular member generally indicated at 110 formed from a generally rectangular sheet of material 112 having a proximal end 114 and a distal end 116. The sheath is coiled to form a tubular structure with the inner edge 120 of the sheet being overlapped by the outer edge 118. The overlap is continuous along the full longitudinal dimension. Thus, the coiled tubular sheath is of uniform diameter in its native unexpanded state, since the tubular sheath, if unrolled and lying in a flat form, has the shape of a rectangular sheet.

Figure 2:
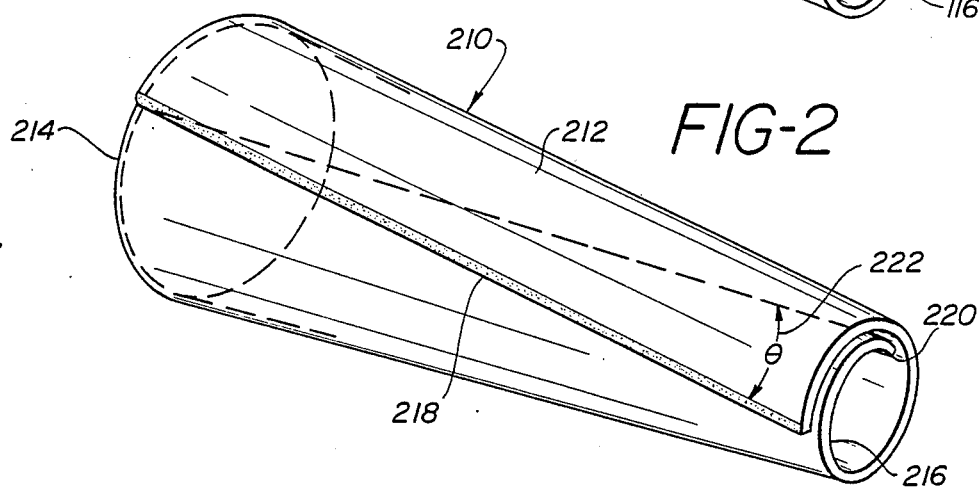

A second, alternate embodiment is shown in FIG. 2 and possesses a longitudinal coil with the degree of overlap increasing progressively from the proximal end to the distal end. The device generally indicated at 210 is made from a sheet of material 212 and has a proximal end 214 and a distal end 216. The inner edge 220 is overlapped by the outer edge 218 to form a conical or tubular body. The angle of taper 222 can be discerned from the angle formed by the inner edge 220 and the outer edge 218. Since the uncoiled sheath is a rectangular sheet, progressively increasing the extent of coil and overlap along the longitudinal dimension causes a tapering 222 of the sheath's diameter in the configuration of a cone. Thus, in the unstressed native state, the sheath tapers over its entire length, and its diameter is least at the tip 216. Thus, such a sheath may cooperate with a new type of introducing-dilating catheter, i.e. one that tapers over a considerable length, such as 100 mm., rather than over the shorter length of 20 mm., which is referred to as the tip in present state of the art of introducing-dilating catheters.

Figure 3:
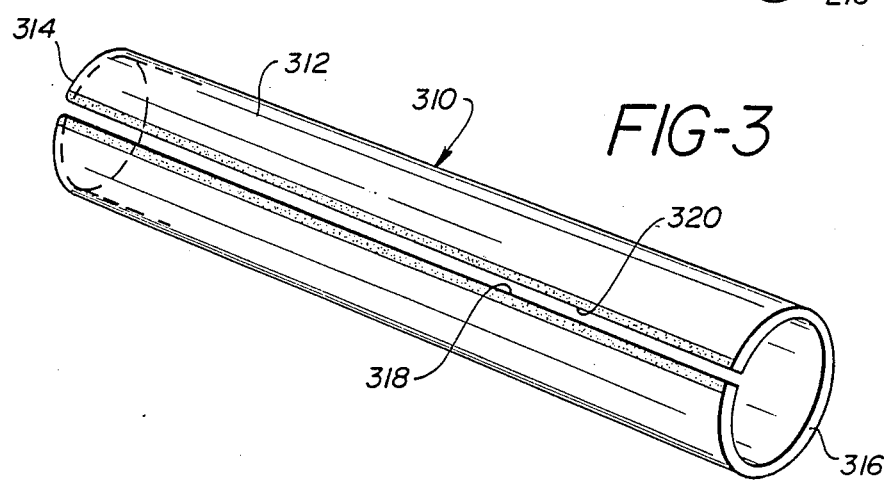

In the next embodiment shown in FIG. 3, variability of the internal diameter is not needed so that the sheath generally indicated at 310 is a sheet 312 with a single longitudinal seam formed by the edges 320 and 318 of the sheet. As before, the sheath has a distal end 316 and a proximal end 314.

Since variability of internal diameter is not needed, the sheath 312 may be fabricated without coiling or overlap of the edges. This simpler embodiment retains the ability to completely remove the sheath easily and without requiring two hands.

FIG. 4 shows another embodiment of the invention having an attachment fitting for attaching the sheath to various connecting lines. As shown in FIG. 4, a sheath similar to the type shown in FIG. 1, generally indicated at 410, is made from a rectangular sheet 412 having a proximal end 414 and a distal end 416. The outer edge 418 overlaps the inner edge 420. Attached to the proximal end is an attachment fitting generally indicated at 424 which fitting is in the form of a LUER-LOK type fitting. The fitting has a hub 427 which is fastened to the proximal outer surface of the sheet 412, and a rear portion 429 extending radially from the proximal end of the sheath. The radially extending portion 429 includes LUER ears or tabs 425 on the end thereof, which ears or tabs connect with the coacting LUER fitting on the conduit to provide communication with a conduit means to the sheath.

A slit 426 runs through hub 427 and radially extending portion 429 from the central bore 428 of the fitting to the edge of the fitting and allows the fitting to expand when the proximal end of the sheath is expanded. This is best shown in FIGS. 5 and 6.

As seen in FIG. 5, the end portion 430 between the inner edge 420 of the sheath and the slit 426 of the attachment fitting is unconnected to the attachment fitting. All the remainder of the proximal end 414 is connected to the attachment fitting.

As shown in FIG. 6, when it is desired to expand the sheath, the attachment fitting can deform to accommodate the expansion of the sheath so that the inner edge 420 will approach the outer edge 418.

FIG. 7 shows another embodiment of the invention similar to that of FIGS. 4, 5 and 6 but with a tapered sheath. In this case, the tapered sheath with an attachment fitting, shown in a more general form, is generally indicated at 710. It is made from a rectangular sheet of material 712 and has a proximal end 714 and a distal 716. The sheet 712 has an outer edge 718 and an inner edge 720 which overlap. The portion of overlap is indicated at 730 and it varies along the length of the sheath in accordance with the angle of taper 722. The attachment fitting 724 has a slit 726 which extends from the edge of the attachment fitting to the bore in the attachment fitting 728.

The tapered sheath with an attachment fitting 710 is constructed so that the inner and outer edges 720 and 718, respectively at the proximal end 714, which are connected to the attachment fitting 724, will exactly meet at the slit 726 so that there will be no overlap at that point. In the relaxed state, the sheath will have an angle of taper, generally indicated at 722.

The distal end of the sheath 716 can be adjusted in size as well as the angle of taper by rotating the sheath once the sheath is within the percutaneous incision. Rotating the sheath in the direction of the arrow will cause the overlap to increase, reducing the area of the distal end, whereas rotating the sheath in the direction opposite the arrow will tend to cause the overlap between the inner and outer edges 720 and 718 to decrease, thereby enlarging the diameter of the distal end. Therefore, once a catheter has been introduced through the bore 728 of the sheath, if there is any problem as far as the sheath being too tight, rotation of the sheath counter to the direction of the arrow will free-up the sheath so that the catheter can be more easily passed through the sheath. Once the catheter is passed through the distal end of the sheath, the sheath can then be rotated in the direction of the arrow to tighten the sheath around the catheter and therefore minimize or seal blood loss from the space between the sheath and the catheter.

The connecting fittings can be of a general nature, as shown in FIG. 7, or they can be of a more specific type such as a LUER-LOK type fitting, as, for example, the LUER type fitting (in this case of the female configuration), normally associated with catheters or needles for connecting the needles or catheters to other conduits to maintain fluid communication between the lumen of the needle and/or catheter with another connecting device.

Figure 8:
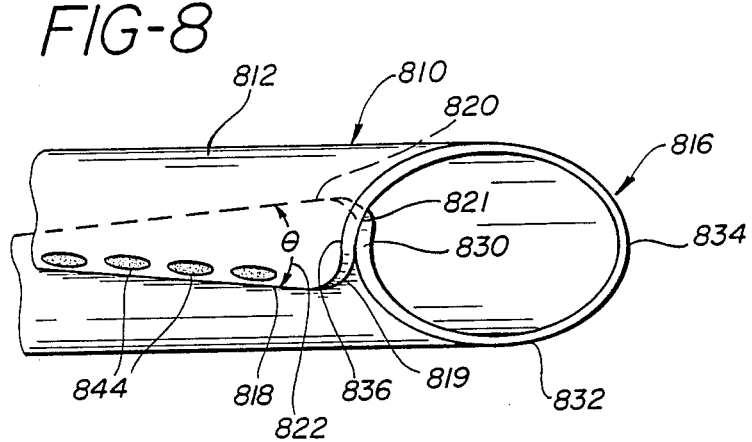
FIG. 8 is a top view of another embodiment of the invention having a bevelled tip.
Figure 9:
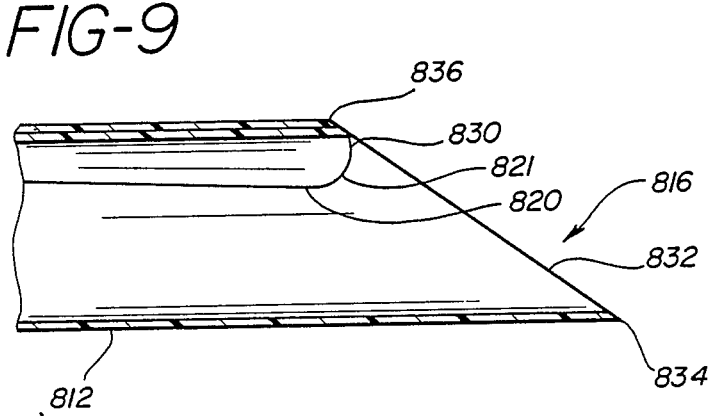
FIG. 9 is a section of FIG. 8.

FIGS. 8 and 9 show another embodiment of the invention. In this case, FIGS. 8 and 9 show a partial view, FIG. 8 from the top and FIG. 9 a section of FIG. 8. FIG. 8 shows a partial view of a catheter similar to that shown in FIG. 2 in which the catheter has a bevelled tip at the distal end to ease the insertion of the catheter. As shown, the catheter, generally indicated at 810 is made from a sheath 812 having a proximal end and a distal end 816. The sheet 812 has an outer edge 818 which overlaps inner edge 820.

The outer edge 818 has a rounded distal corner 819 and the inner edge 820 has a rounded distal corner 821. The rounded corners are formed to eliminate sharp points at the edges of the sheath which could damage abutting tissue. Of course, though shown and discussed only for the embodiment of the invention in FIGS. 8 and 9, it is understood that all embodiments of the invention could have rounded distal inner and outer edges.

The angle of taper is indicated at 822. Of course, if the edges 818 and 820 are not parallel when sheet 812 is projected flat, then the angle 822 between the edges would not be truly representative of the angle of taper. However, if the edges 818 and 820 are parallel when sheet 812 is flat, then 822 will be representative of the angle of taper.

The distal end 816 of sheath 812 is formed into a bevelled tip, generally indicated at 832. The bevelled tip has an entry leading edge 834 and a rearmost portion 836. The overlapping portion of the material between the inner edge 820 and the outer edge 818 is indicated as 830. The outer edge 818 intersects the bevelled tip 832 near the rearmost portion 836 of the tip. The outer edge 818 of the sheath may be marked with visual indicators 844 to assist in the location of the seam. Also, by knowing where the intersection of the outer edge 818 with the rear of the bevelled tip, it is easy to identify the position of the rear of the bevelled tip.

While FIGS. 8 and 9 show a catheter having an angle of taper 822, it is also possible for any of the embodiments shown in FIGS. 1, 2, 3, 4 and 7 to also employ a bevelled tip.

Figure 10:
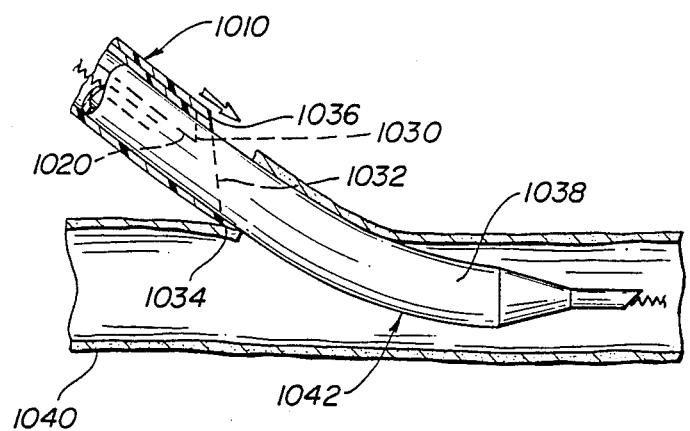
FIGS. 10, 11 and 12 show sequential introduction of a sheath and catheter into a vessel.
Figure 11:
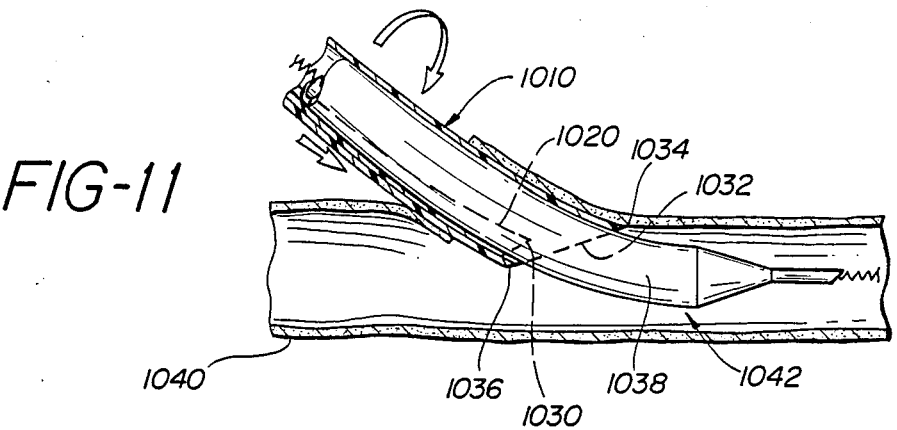
Figure 12:
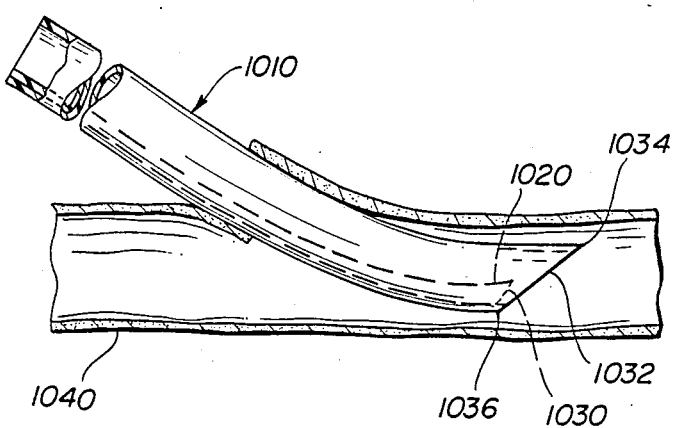

FIGS. 10, 11 and 12 show a sheath similar to the sheath shown in FIGS. 8 and 9 being used in conjunction with an introducing catheter. The sheath, generally indicated at 1010, has a bevelled tip 1032 with a leading edge 1034 and a rear end 1036. An introducing catheter 1038 is positioned within the lumen 1042 of the vessel 1040.

Initial penetration of the sheath 1010 is made with the leading edge 1034 in the lowermost position. After the rear end 1036 has passed through the incision in the vessel 1040 and entered the lumen 1042 of the vessel, tee sheath and catheter are rotated as a unit in the direction as would tighten the distal end of the sheath about the catheter. This rotation continues until the leading edge 1034 is now in the uppermost position and the rear end 1036 is in the lower position. The sheath can then be advanced directly down into the vessel without fear of the sharp leading edge 1034 puncturing the rear wall of vessel 1040 or abrading the rear wall of the vessel.

The technique for introducing the bevelled catheter is shown in greater detail in my co-pending application, Ser. No. 071,040, filed July 8, 1987, the specification of which is incorporated herein by reference.

To remove any of the sheaths described is a simple operation. Since the sheaths are shaped and held together only by the residual elasticity of the memory of the material, the proximal end with the mechanical fitting can be expanded so that the catheter begins to emerge through the seam between the inner and outer edges of the sheath. Withdrawing of the sheath further causes the catheter to slide through and along the seam thereby expanding the seam as needed for removal of the sheath from the catheter. The inherent memory of the sheath will cause it to return to its original configuration after the catheter has been removed.

Similarly, if it is ever desired to place the sheath onto a catheter where none has been in position, or where there was a sheath originally positioned but which has been removed, it is possible to install a new sheath by merely spreading the edges of the sheath to be installed at the distal tip of the sheath so that the distal tip can be inserted around the catheter. A progressive insertion of the sheath or movement of the sheath with respect to the catheter causes the catheter to find its way through the seam of the sheath into the interior lumen of the sheath.

If the sheath have a connecting fitting whether of the general type, as shown in FIG. 7, or the specific type as shown in FIG. 4, the fitting will offer no hindrance to insertion or removal of a catheter throught the wall of the sheath. Since the fitting itself is made of flexible, preferably resilient, material, all that is necessary is to spread the seam of the fitting for either the entry or removal of the device from the lumen of the sheath.

The sheath, if it has a bevelled end, can then be introduced by the technique described in FIGS. 10, 11 and 12 or conversely if it is the type having a more common distal end merely positioned or insinuated into the incision of the vessel in a standard manner.

As mentioned previously, the size of the sheath can be easily varied, especially if the sheath is of the tapered form. If the sheath has a connective fitting, this is even easier by merely grasping the fitting and rotating the sheath so that the edges of the incision of the vessel will tend to either spread the sheath wider or narrow the diameter of the sheath, depending upon the direction of rotation.

It should be noted with respect to the expandable sheaths shown that it would be possible for the sheaths to operate as a guide for catheters and other equipment through incisions into the lumen of a vessel even if the edges of the sheath did not always meet. So, for example, it is possible for the sheath as shown in FIG. 3 and 4 to be expanded to accommodate an implement that is larger than the diameter of the sheath. Similarly, it would be capable for this to occur with respect to sheaths which are tapered or have bevelled tips.

Having thus described my invention in detail, it is understood that the foregoing description is not intended to limit the spirit and scope thereof. What is desired to be protected by Letters Patent is set forth in the appended claims.

What is claimed is:

1. A removable sheath sized and intended for insertion into a blood vessel comprising:
   a tubular structure formed of a flexible material with memory to return to an original configuration and when enlarged to maintain a closely conforming relationship to a cylindrical body for receiving a catheter therein and having a longitudinal seam formed along its entire length for permitting said structure to expand to accommodate catheters of different diameters and to allow removal of a catheter through said longitudinal seam;
   portions of said tubular structure being capable of overlapping each other at said seam;
   said structure having a distal end and a proximal end, connecting means affixed to said proximal end for coupling said structure to other devices, said connecting means including a slit formed therein colinear with said seam to allow for removal of a catheter through said slit.

2. The sheath of claim 1 wherein said overlapping portion are equal along the length of said seam.

3. The sheath of claim 1 wherein said overlapping portions are unequal along the length of said seam so that said tubular structure forms a conical shape.

4. A removable sheath sized and intended for insertion into a blood vessel comprising:
   a tubular structure formed of a flexible material with memory to return to an original configuration and when enlarged to maintain a closely conforming relationship to a cylindrical body for receiving a catheter therein and having a longitudinal seam formed along its entire length for permitting said structure to expand to accommodate catheters of different diameters;
   portions of said tubular structure being capable of overlapping each other at said seam;
   said structure having a distal end and a proximate end, connecting means affixed to said proximal end for coupling said structure to other devices, said connecting means including a slit formed therein colinear with said means;
   said structure has at least one longitudinal edge on the outer surface thereof defining said seam;
   and wherein said structure has a distal end and a proximal end and further including a bevel cut at said distal end.

5. The sheath of claim 4 wherein the rearmost portion of the bevel is located at said longitudinal edge of said sheath.

6. A removable sheath for inserting a catheter into a blood vessel comprising:
a tubular structure formed of a flexible material with memory for receiving a catheter therein, said tubular structure having a longitudinal seam formed along its entire length for permitting said structure to expand as a function of the diameter of the catheter, and having a distal end and a proximal end;
said tubular structure having a longitudinal edge on the outer circumference thereof forming said seam;
connector means coupled to said proximal end for enabling the tubular structure to be coupled to other devices; and
a bevelled portion cut diagonally in said distal end.

7. A fitting for connecting a sheath to a conduit comprising:
a sheath formed of a flexible material with memory to return to an original configuration and when enlarged to maintain a closely conforming relationship to a cylindrical body for receiving a catheter therein;
engaging means extending radially from the sheath;
fastening means fastening said engaging means to said sheath; and
slit means extending axially the length of said fastening means and radially from the perimeter of said fitting for connecting said sheath to the innermost surface of said fitting;
said fitting being made from flexible material to allow the fitting to be opened along said slit means;
said fitting means comprising hub means fastened to the external surface of said sheath; and said engaging means extends radially outward from said hub means.

8. A method for inserting and adjusting a sheath for use in conjunction with the introduction of catheters into the body comprising the steps of:
disposing a sheath formed of a flexible material with memory to return to an original configuration and when enlarged to maintain a closely conforming relationship to a cylindrical body for receiving a catheter therein having a longitudinal seam extending along its length and overlapping portions at said seam about a catheter to move with the catheter;
inserting the catheter into a passage formed in the body;
advancing the catheter until the distal end of the of the sheath is fully entered into the passage formed in the body; and
adjusting the diameter of the sheath within the passage formed in the body by enlarging or reducing the diameter of the space occupied by the catheter and allowing the resilience of the sheath to conform to the space occupied by the catheter by rotating the sheath to allow said overlapping portions of the sheath to be enlarged or reduced in accordance with the direction of rotation.

9. A method for removing a catheter from a sheath disposed within a passage within the body comprising the steps of:
maintaining the sheath stationary;
spreading the sheath formed of a flexible material with memory to return to an original configuration and when enlarged to maintain a closely conforming relationship to a cylindrical body for receiving a catheter therein along a seam to open the sheath; and
removing the catheter through the seam in the sheath while holding the sheath stationary and withdrawing the catheter from the sheath thereby allowing the catheter to find its way through the seam.

10. A method for inserting a catheter into a sheath disposed within a passage within the body comprising the steps of:
spreading a sheath formed of a flexible material with memory to return to an original configuration and when enlarged to maintain a closely conforming relationship to a cylindrical body for receiving a catheter therein along a seam to open the sheath;
inserting a catheter through the seam of the sheath until the catheter is disposed in the desired position in the passage within the body; and
spreading a connecting fitting attached to the sheath along a slit formed in the fitting to allow for passage of the catheter through the wall of the connecting fitting.

11. A method for inserting and adjusting a sheath for use in conjunction with the introduction of catheters into the body comprising the steps of:
disposing a sheath formed of a flexible material with memory to return to an original configuration and when enlarged to maintain a closely conforming relationship to a cylindrical body for receiving a catheter therein having a longitudinal seam extending along its length and overlapping portions at said seam about a catheter to move with the catheter;
the disposing of the sheath about the catheter including the step of spreading a connecting fitting attached to the sheath along a slit in the connecting fitting to allow for insertion of the catheter through the wall of the fitting and thereby into the sheath;
inserting the catheter into a passage formed in the body;
advancing the catheter until the distal end of the sheath is fully entered into the passage formed in the body; and
adjusting the diameter of the sheath within the passage formed in the body by enlarging or reducing the diameter of the space occupied by the catheter and allowing the resilience of the sheath to conform to the space occupied by the catheter by rotating the sheath to allow said overlapping portions of the sheath to be enlarged or reduced in accordance with the direction of rotation.

12. A method for removing a catheter from a sheath disposed within a passage within the body comprising the steps of:
spreading a sheath formed of a flexible material with memory to return to an original configuration and when enlarged to maintain a closely conforming relationship to a cylindrical body for receiving a catheter therein along a seam to open the sheath;
removing the catheter through the seam in the sheath while holding the sheath stationary and withdrawing the catheter from the sheath thereby allowing the catheter to find its way through the seam; and
spreading a connecting fitting attached to the sheath along a slit formed in the fitting to allow for passage of the catheter through the wall of the connecting fitting.

13. A removable sheath sized and intended for insertion into a blood vessel comprising:
a tubular structure formed of a flexible material;

said tubular structure having a seam therein extending axially the length of a tubular structure;

said material forming said tubular structure having memory to return to an original configuration so that when enlarged it will maintain a closely conforming relationship to a cylindrical body in order to receive a catheter therein thereby permitting said tubular structure to expand to accomodate catheters of different diameters and to enable said tubular body to completely circumferentially conform along a given axial region to an internal catheter disposed within said tubular body; and said seam having edges which coact to enable insertion and removal of a catheter through said seam.

14. A removal sheath sized and intended for insertion into a blood vessel comprising:

a tubular structure formed of a flexible material;

said tubular structure having a seam therein extending axially the length of the tubular structure;

said material forming said tubular structure having memory to return to an original configuration so that when enlarged it will maintain a closely conforming relationship to a cylindrical body in order to receive a catheter therein thereby permitting said tubular structure to expand to accommodate catheters of different diameters and to enable said tubular body to completely circumferentially conform along a given axial region to an internal catheter disposed within said tubular body;

said seam having edges which coact to enable insertion and removal of a catheter through said seam; and said tubular structure having a distal end and a proximal end, the tubular structure formed so as to taper downward from the proximal end to the distal end in a conical fashion.

15. The sheath of claim 13, wherein portions of said tubular structure are capable of overlapping each other at said seam.

16. The sheath of claim 13, 14, or 15 having visible indicia means marking said seam along its entire length to ensure said seam is visible.

17. A removable sheath sized and intended for insertion into a blood vessel comprising:

a tubular structure formed of a flexible material;

said tubular structure having a slit therein extending axially the length of the tubular structure;

said material forming said tubular structure having memory to return to an original configuration so that when enlarged it will maintain a closely conforming relationship to a cylindrical body in order to receive a catheter therein thereby permitting said tubular structure to expand to accommodate catheters of different diameters and to enable said tubular body to completely circumferentially conform along a given axial region to an internal catheter disposed within said body; and further comprising connection means affixed to said proximal end for coupling said structure to other devices, said connecting means including a slit formed therein colinear with said seam.

18. A removable sheath sized and intended for insertion into a blood vessel comprising:

a tubular structure formed of a flexible material;

said tubular structure having a slit therein extending axially the length of the tubular structure;

said material forming said tubular structure having memory to return to an original configuration so that when enlarged it will maintain a closely conforming relationship to a cylindrical body in order to receive a catheter therein thereby permitting said tubular structure to expand to accommodate catheters of different diameters and to enable said tubular body to completely circumferentially conform along a given axial region to an internal catheter disposed within said tubular body;

said tubular structure having a distal end and a proximal end, the tubular structure formed so as to taper downward from the proximal end to the distal end in a conical fashion; and connection means affixed to said proximal end for coupling said structure to other devices, said connecting means including a slit formed therein colinear with said seam.

19. A removable sheath sized and intended for insertion into a blood vessel comprising:

a tubular structure formed of a flexible material;

said tubular structure having a slit therein extending axially the length of the tubular structure; and said material forming said tubular structure having memory to return to an original configuration so that when enlarged it will maintain a closely conforming relationship to a cylindrical body in order to receive a catheter therein thereby permitting said tubular structure to expand to accommodate catheters of different diameters and to enable said tubular body to completely circumferentially conform along a given axial region to an internal catheter disposed within said tubular body;

wherein portions of said tubular structure are capable of overlapping each other at said seam; and further comprising connection means affixed to said proximal end for coupling said structure to other devices, said connecting means including a slit formed therein colinear with said seam.

20. The sheath of claim 17, 18, or 19 wherein said connecting means comprise:

hub means fastened to the external surface of said sheath; and engaging means extending radially outward from said hub means.

* * * * *